United States Patent [19]

Leap

[11] Patent Number: 5,106,379
[45] Date of Patent: Apr. 21, 1992

[54] SYRINGE SHIELDING ASSEMBLY

[76] Inventor: E. Jack Leap, 35605 E. Truman Rd., Oak Grove, Mo. 64075

[21] Appl. No.: 682,649

[22] Filed: Apr. 9, 1991

[51] Int. Cl.[5] .............................................. A61M 5/32
[52] U.S. Cl. ..................................... 604/198; 604/263
[58] Field of Search ............. 604/198, 263, 192, 110, 604/218, 187

[56] References Cited

U.S. PATENT DOCUMENTS

| | | | |
|---|---|---|---|
| 4,573,976 | 3/1986 | Sampson | 604/198 |
| 4,664,654 | 5/1987 | Strauss | 604/198 |
| 4,693,708 | 9/1987 | Wanderer et al. | 604/198 |
| 4,702,738 | 10/1987 | Spencer | 604/198 |
| 4,723,943 | 12/1987 | Spencer | 604/198 |
| 4,737,144 | 4/1988 | Choksi | 604/198 |
| 4,755,369 | 10/1988 | Schwartz | 604/198 |
| 4,767,413 | 8/1988 | Haber et al. | 604/198 |
| 4,801,295 | 1/1989 | Spencer | 604/198 |
| 4,813,940 | 3/1989 | Parry | 604/198 |
| 4,850,968 | 7/1989 | Romano | 604/110 |
| 4,850,977 | 7/1989 | Bayless | 604/198 |
| 4,874,283 | 10/1989 | McNaughton | 604/198 |
| 4,900,311 | 2/1990 | Stern et al. | 604/198 |
| 4,911,693 | 3/1990 | Paris | 604/198 |
| 4,917,673 | 4/1990 | Coplin | 604/198 |
| 4,923,447 | 5/1990 | Morgan | 604/198 |
| 4,955,868 | 9/1990 | Klein | 604/198 |
| 4,966,592 | 10/1990 | Burns et al. | 604/198 |

Primary Examiner—John D. Yasko
Attorney, Agent, or Firm—Litman, McMahon & Brown

[57] ABSTRACT

A syringe having a sheath that is slidingly received on a barrel of the syringe so as to be movable between a retracted needle exposing position and an extended needle surrounding position. A boss fixedly attached to the syringe barrel cooperates with an L-shaped bayonet slot in the sheath to guide the cylindrical sheath. The sheath is connected to the syringe by a coil spring which biasingly urges the sheath into the extended needle surrounding position. The sheath is connected to the coil spring such that as the sheath is advanced from the retracted position to the extended position, the spring biasingly rotates the sheath with respect to the barrel such that the boss is advanced into a laterally extending portion of the slot so as to prevent accidental compression of the sheath. When the sheath is advanced to the retracted position a barb on the barrel cooperates with a barb receiving aperture in the sheath to restrain the sheath in the retracted position. A trigger on the sheath is engageable by a user to release the sheath from the retracted position.

10 Claims, 1 Drawing Sheet

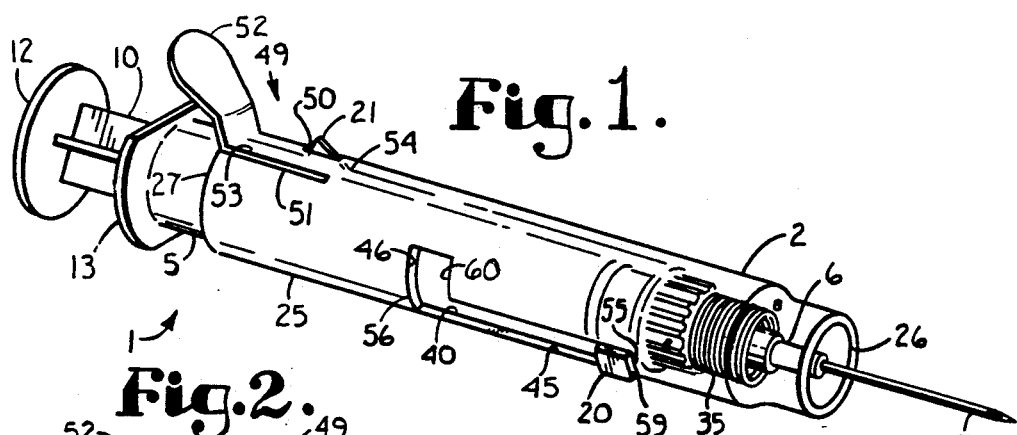
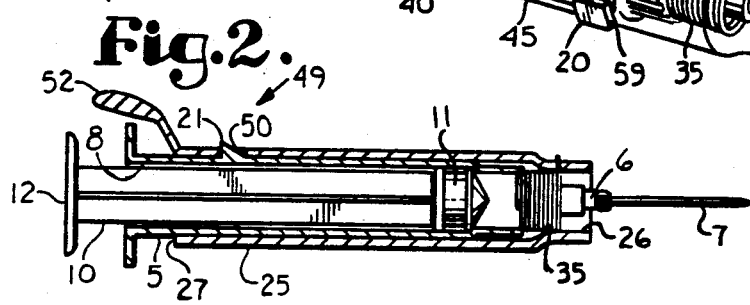
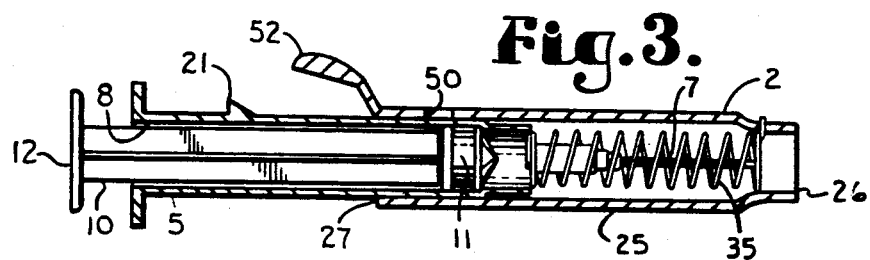
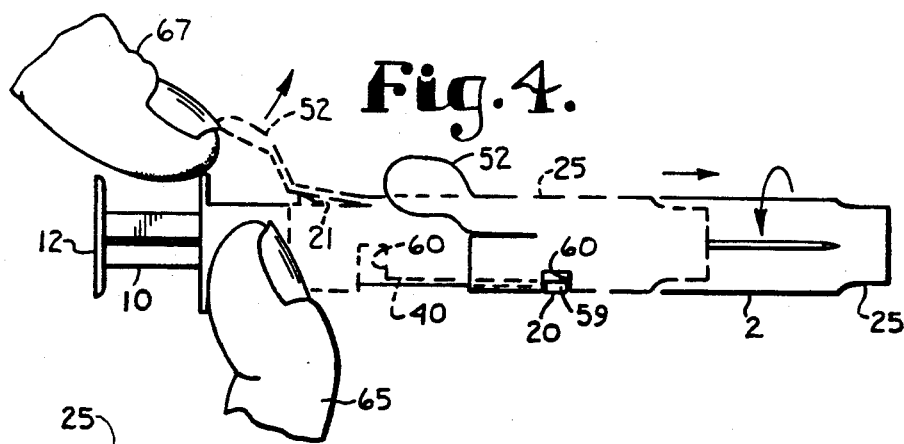
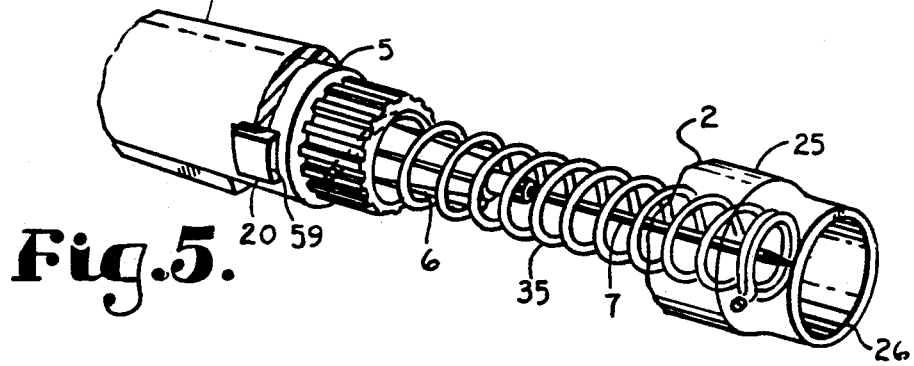

SYRINGE SHIELDING ASSEMBLY

BACKGROUND OF THE INVENTION

The present invention relates generally to disposable syringes and in particular to a shielding assembly for preventing accidental needle pricks.

The spread of Acquired Immune Deficiency Syndrome or AIDS in the 1980's, has greatly increased the concerns of health care providers over the spread of communicable diseases through accidental needle pricks. Nurses, doctors and other health care providers accidentally prick themselves with needles on an average of two or more times a year. With the increase in AIDS, the chance of such a health care provider being pricked by an AIDS contaminated needle over a period of years has become quite high. Further, other severe but less deadly diseases, such as hepatitis, are transmitted through contaminated needle pricks. Such pricks occur in many ways, such as a nurse tripping while carrying a used and exposed needle or even while trying to cap a used needle.

Consequently, a greater need has developed for shielding devices for needles of syringes such that the shielding devices are effective, easy to use and require only minor modifications to allow use with conventional types of disposable syringes. Numerous devices have been developed to reduce the risk of accidental needle pricks.

Many of these devices include a cylindrical sheath secured to the syringe which may be telescopically advanced and retracted to enclose and expose the needle of the syringe. The currently available shielding devices providing a cylindrical sheath to telescopically encircle the needle of a syringe suffer several shortcomings. Many of the existing devices require an operator to use both hands to position the protective sheath in encircling relation with the syringe needle thereby increasing the likelihood of accidental needle pricks. That is, when the user reaches with one hand to extend the sheath of the syringe being held by the other hand, the user accidentally sticks the free hand through carelessness, being bumped, or the like.

In many of the existing devices, the protective sheath cannot be locked in encircling relationship with the syringe needle possibly resulting in accidental needle pricks if a compressive force is inadvertently applied to the protective sheath. In other existing devices the protective sheath permanently locks in protective relationship with the syringe needle when advanced thereto preventing intermediate protection of the syringe needle where the syringe must be used more than once for a given procedure. Existing shielding devices also tend to require major modifications to existing syringes or greatly interfere with the normal use of the syringe.

SUMMARY OF THE INVENTION

The present invention provides an improved syringe for reducing the risk of accidental needle pricks. A standard type of syringe having a barrel with a plunger slidably receivable in one end and a needle secured to an opposite end further includes, in accordance with the present invention, a cylindrical sheath or sleeve attached to the barrel. The sheath is telescopically located relative to the barrel of the syringe and releasably held in a retracted position by a retraction locking means or a latch. A spring interconnects the barrel to the sheath and biases the sheath into encircling or surrounding relationship with respect to the needle of the syringe when the latch is released by a user. The sheath may be retracted by a user over the barrel so as to fully expose the needle by a user pushing against the spring until the latch relatches.

A boss or protrusion extending from the barrel cooperates with an L-shaped bayonet slot in the sheath to form extension locking mean for locking the sheath in surrounding relationship with the needle of the syringe. The L-shaped bayonet slot is positioned on the sheath such that a laterally extending portion of the slot is located in spaced relationship relative to the front end of the sheath.

As the sheath is biased into surrounding relationship to the needle, the boss advances along the L-shaped bayonet slot to the laterally extending portion of the slot. The sheath is secured to the barrel by the spring such that as the boss reaches the laterally extending portion of the slot, the spring also biases the sheath to rotate so that the boss is urged into the laterally extending portion of the slot. With the boss positioned within the laterally extending portion of the slot a compressive force alone will not cause the sheath to advance out of surrounding relationship with the needle.

To transfer the sheath out of surrounding relationship with the needle, the sheath must first be rotated by manual pressure exerted by the user against the twisting force of the spring out of the laterally extending portion of the slot. The sheath may then be retracted, again by manipulation and manual pressure exerted by the user, against the force of the spring to expose the needle.

When the sheath is fully retracted a barb of the latch on the barrel of the syringe cooperates with a barb receiving aperture in the sheath to secure the sheath in the retracted position against the biasing force of the spring. The latch includes a trigger release associated with the barb receiving aperture on the sheath that is operable to overcome the cooperation between the barb and the barb receiving aperture so as to release the barb and attached sheath and such that the sheath is biased into surrounding relationship with the needle. Again, as the sheath is biased into surrounding relationship with respect to the needle, the spring rotates the sheath so that the boss is advanced into engaging relationship with the laterally extending portion of the bayonet slot thereby locking the sheath in surrounding relationship with respect to the needle.

OBJECTS AND ADVANTAGES OF THE INVENTION

Therefore the objects of the present invention are: to provide an improved syringe that operates to reduce the risk of accidental needle pricks; to provide such a syringe that includes a cylindrical sheath which is slidably advanceable from an extended, needle encircling relationship with the syringe to a retracted, needle exposing relationship with the syringe; to provide such a syringe having extension locking means for locking the sheath in the extended, needle encircling relationship; to provide such a syringe having retraction locking means for locking said sheath in said retracted, needle exposing relationship with the syringe; to provide such a syringe having means for manually overcoming said retraction locking means and bias means for automatically advancing said sheath into encircling relationship with said needle; to provide such a syringe having means for manually overcoming said extension locking means; to provide such a syringe that does not interfere with the normal use of the syringe; to provide such a syringe which requires minimal use of two hands to operate and especially can be operated and placed in a needle protected configuration by use of a single hand; to provide such a syringe that requires minimal modifications to conventional syringes; to provide such a syringe that is relatively inexpensive to manufacture, easy to use and particularly well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of the syringe according to the present invention including a cylindrical sheath.

FIG. 2 is a cross-sectional view of the syringe on a reduced scale, taken along line 2—2 of FIG. 1 showing the sheath in a retracted position.

FIG. 3 is a cross-sectional view similar to that of FIG. 2 showing the cylindrical sheath in an extended needle surrounding relationship with respect to the syringe.

FIG. 4 is a side elevational view of the syringe showing the cylindrical sheath in phantom lines in the retracted position with the needle exposed and in solid lines in the extended needle surrounding relationship with the syringe.

FIG. 5 is an enlarged and fragmentary perspective view of the syringe with portions broken away to show interior detail.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally represents a syringe incorporating a shielding assembly 2 according to the present invention. The shielded syringe 1 generally comprises a hollow, cylindrical syringe barrel 5, a needle hub 6 and a needle 7. The needle 7 is secured to a front end of the barrel 5 by the needle hub 6. The barrel 5 includes an internal chamber 8. A plunger 10, having a rubber plug 11 secured to one end thereof is slidingly receivable within the chamber 8 of the barrel 5 from a rear end thereof such that the rubber plug 11 extends into the barrel 5.

The end of the plunger 10 opposite the rubber plus 11 is flattened to form a thumb engaging surface or thumb rest 12 which is engageable by a user's thumb to advance the plunger 10 into the barrel 5 so as to force the contents of the barrel 5 out of the needle 7. The rear end of the barrel 5 includes a set of oppositely directed finger flanges 13 which are generally grasped by a user's index and middle finger when using the syringe 1.

The outer surface of the barrel 5 of the syringe 1 is modified, as compared to conventional syringes, by the addition of a rectangular boss 20 and a barb 21. The rectangular boss 20 is positioned on the outer surface of the barrel 5 near the front end of the barrel 5 and the barb 21 is generally positioned on the outer surface of the barrel 5 near the rear end of the barrel 5.

A cylindrical sheath 25, having a front open end 26 and a rear open end 27, is slidingly secured over the cylindrical barrel 5 such that the cylindrical sheath 25 is advanceable from a retracted needle exposing position, as seen in FIG. 2, to an extended needle surrounding position wherein the needle 7 is protected by the sheath 25 from accidentally pricking a user, as is seen in FIG. 3. When in the needle surrounding position, the sheath cannot be retracted by normal forces, such as being bumped, acting axially against the sheath 25. As will be discussed below, a user can retract the sheath 25 by both rotating the sheath 25 and applying an axial force against the sheath 25 simultaneously. A coil spring 35, secured at one end to the needle hub 6 of the syringe 1 and at an opposite end to the cylindrical sheath 25 near the front open end 26, biases the cylindrical sheath towards the extended needle surrounding position.

The cylindrical sheath 25 includes an L-shaped bayonet slot 40 generally extending lengthwise and parallel to the central axis of and along a substantial portion of the cylindrical sheath 25 which is positioned on the cylindrical barrel 5 such that the rectangular boss 20 is slidingly disposed within the bayonet slot 40. The bayonet slot 40 includes a longitudinal portion 45 and a laterally extending portion 46. The longitudinal portion 45 extends lengthwise across a portion of the cylindrical barrel 5 and the laterally extending portion 46 extends perpendicularly to the longitudinal portion 45 so as to be located circumferentially with respect to the cylindrical sheath 25 near the rear open end 27 thereof.

The cylindrical sheath 25 further includes a barb receiving aperture 50 positioned near the rear open end 27 of the cylindrical sheath 25 and adapted to encircle the barb 21 and form a latch 49 when the cylindrical sheath 25 is positioned in the retracted needle exposing position, as seen in FIG. 2, so as to function as restraining or locking means restraining the cylindrical sheath 25 in such a retracted position against the biasing force of the coil spring 35. A pair of slits 51 extend lengthwise along the cylindrical sheath 25 from the rear open end 27 thereof on opposite sides of the barb receiving aperture 50 so as to form a tab 53 that is swingable upon a hinge portion 54. Normally, the tab 53 is located so as to align with the remainder of the sheath and is resiliently urged to do so by means of the materials of construction. However, the tab 53 can be raised by swinging radially outward about the hinge portion 54. The barb receiving aperture 50 is located within the tab 53. A trigger 52, integrally formed with the tab 53 and the cylindrical sheath 25, extends rearwardly from the rear open end 27 of the cylindrical sheath 25 between the slits 51.

The trigger 52 generally functions as release means and is engageable by a user of the syringe 1 to bias the tab 53 between the slits 51, including the barb receiving aperture 50, outwardly and away from the cylindrical barrel 25 and the barb 21 so as to remove the barb receiving aperture 50 from surrounding relationship with respect to the barb 21 so as to allow the coil spring 35 to advance the cylindrical sheath 25 from the retracted needle exposing position to the extended needle encircling position. As the cylindrical sheath 25 advances from the retracted position to the extended position, the boss 20 advances along the longitudinal portion 45 of the L-shaped bayonet slot 40 from a front end 55 to a rear end 56 thereof.

An important aspect of the present invention is that the coil spring 35 is twisted upon assembly of the syringe 1 so as to apply a continuous torque to the sheath 25 relative to the barrel 5. That is, when viewed from the needle end, the sheath 25 will be continuously biased to rotate counterclockwise with respect to the barrel 5. In this manner, the boss 20 is urged into the laterally extending portion 46 of the slot 40 whenever both are aligned. In particular, the cylindrical sheath 25 is secured to the cylindrical barrel 5 by the coil spring 35 such that when the cylindrical sheath 25 is advanced to the extended needle surrounding position so that the boss 20 is advanced to the rear end 56 of the longitudinal portion 45 of the slot 40 so as to be aligned with the laterally extending portion 46 of the slot 40, the cylindrical sheath 25 is rotated with respect to the cylindrical barrel 5 by the coil spring 35 so that the boss 20 is advanced into the laterally extending portion 46 of the slot 40.

If a compressive force is applied to the cylindrical sheath 25 when the boss 25 is biasingly positioned within the laterally extending portion 46 of the slot 40, an abutting edge 59 of the boss 20 engages a lateral slot edge 60 on the cylindrical sheath 25 so as to prevent retraction of the cylindrical sheath 25 thereby reducing the likelihood of accidental needle pricks. The spring 35 holds the sheath 25 in the slot portion 46 until the sheath is deliberately manipulated by the user to expose the needle 7. To expose the needle 7, when the cylindrical sheath 25 is in the extended needle encircling position, the cylindrical sheath 25 must first be rotated with respect to the cylindrical barrel 5 so as to advance the boss 20 out of the laterally extending portion 46 of the slot 40. With the boss 20 out of the laterally extending portion 46 of the slot 40, the cylindrical sheath 25 ma be advanced to a retracted needle exposing position by applying a compressive force to the cylindrical sheath 25. When the cylindrical sheath 25 is advanced to the retracted needle exposing position, the barb receiving aperture 50 is captured by and positioned in surrounding relationship with the barb 21 so as to restrain the cylindrical sheath 25 in the retracted position against the biasing force of the coil spring 35.

As shown in FIG. 4, to use the syringe 1, a user preferably grasps the finger flanges 13 with his or her index finger 65 and middle finger (not shown). The thumb 67 of the user is positionable on the thumb rest 12 of the plunger 10 to advance the plunger 10 into the cylindrical barrel 5 to deliver the contents of the syringe 1. The barb 21, the barb receiving aperture 50 and the trigger 52 are positioned on the syringe 1 such that when the cylindrical sheath 25 is in the retracted position, the trigger 52 is generally positioned between the finger flanges 13 such that a user while grasping the finger flanges 13 of the syringe 1 with his or her index finger 65 and middle finger may engage the trigger 52 with his or her thumb 67, as seen in phantom lines in FIG. 4, to remove the barb receiving aperture 50 from encircling relationship with the barb 21 so as to release the sheath 25 and such that the coil spring advances the cylindrical sheath 25 to the extended needle encircling position wherein the boss 20 is advanced into the laterally extending portion 46 of the slot 40 by the coil spring 35.

The cylindrical sheath 25 may be advanced back and forth between the retracted position and the extended position to allow the syringe 1 to be used for multiple injections of the same person, if necessary. The cylindrical sheath 25 is preferably made of a transparent plastic material, similar to that used to make the cylindrical barrels of many syringes, so as to allow a user to view graduated markings (not shown) on the cylindrical barrel 5 of the syringe 1.

It is to be understood that while certain forms of the present invention have been illustrated and described herein, it is not to be limited to the specific forms or arrangement of parts described and shown.

What is claimed and desired to be secured by Letters Patent is as follows:

1. A syringe comprising:
   (a) a cylindrical syringe barrel having a interior chamber; said barrel having a needle secured at a front end and a plunger slidingly received within the interior chamber;
   (b) a boss extending radially outward from said cylindrical syringe barrel;
   (c) a sheath slidingly positioned on said cylindrical syringe barrel and movable between a retracted needle exposing position and an extended needle surrounding position; said sheath having a slot therein to receive said boss; said slot including a longitudinal portion extending parallel to an axis of the syringe barrel and a laterally extending portion extending laterally with respect to said cylindrical syringe barrel and joined to said longitudinal portion;
   (d) a spring biasingly urging said sheath towards the extended needle encircling position; said spring being secured to said cylindrical syringe barrel and said sheath such that said spring biasingly rotates said boss into said laterally extending portion of said slot as said sheath is advanced to said extended needle surrounding position such that when said boss is positioned in said laterally extending portion of said slot said sheath may not be retracted due solely to axial forces acting on said sheath; and
   (e) restraining means for selectively restraining said sheath in said retracted needle exposing position;
   (f) release means for selectively releasing said sheath from said restraining means so as to allow said spring to advance said sheath to said extended needle surrounding position.

2. The syringe as disclosed in claim 1 wherein said restraining means generally comprise:
   (a) a barb fixedly attached to said cylindrical syringe barrel; and
   (b) said sheath includes a barb receiving aperture such that when said sheath is advanced to the retracted needle exposing position said barb receiving aperture captures said barb so as to prevent said sheath from being advanced to the extended needle surrounding position.

3. The syringe as disclosed in claim 2 wherein said release means generally comprise:
   (a) a trigger secured to said sheath and engageable to swing a portion of the sheath including said barb receiving aperture away from said barb such that said barb does not prevent said spring from biasingly urging said sheath to the extended needle surrounding position.

4. The syringe as disclosed in claim 1 wherein:
(a) said spring provides a torque to said sheath relative to said barrel so as to urge said boss into said laterally extending portion of said slot.

5. A syringe comprising:
(a) a cylindrical syringe barrel having a needle secured at a front end and a plunger slidingly received therein;
(b) a boss fixedly attached to said cylindrical syringe barrel;
(c) a barb fixedly attached to said cylindrical syringe barrel;
(d) a sheath slidingly received about said cylindrical syringe barrel and movable between a retracted needle exposing position and an extended needle surrounding position; said sheath having a slot therein to receive said boss; said slot including a longitudinal portion extending axially along said barrel and a laterally extending portion extending laterally with respect to said barrel;
(e) a spring biasingly urging said sheath towards the extended needle surrounding position; said spring being secured t said cylindrical syringe barrel and said sheath such that said spring also biasingly rotates said boss into said laterally extending portion of said slot as said sheath is advanced to said extended needle surrounding position such that when said boss is positioned in said laterally extending portion of said slot said sheath may not be retracted by only forces acting axially against said sheath but such that a user can manually rotate said sheath to allow retraction of said sheath;
(f) said sheath includes a barb receiving aperture positioned thereon such that when said sheath is advanced to the retracted needle exposing position said barb receiving aperture encircles said barb so as to prevent said sheath from being advanced to the extended needle surrounding position; and
(g) said sheath further includes a trigger engageable by a user so as to advance said barb receiving aperture out of encircling relationship with said barb so as to allow said spring to biasingly urge said sheath to the extended needle surrounding position.

6. The syringe as disclosed in claim 5 wherein said sheath is made of a transparent, resilient plastic.

7. The syringe as disclosed in claim 5 wherein said sheath is cylindrical.

8. A syringe comprising:
(a) a cylindrical syringe barrel having a needle secured at a front end and a plunger slidingly received within the barrel; said barrel including a pair of opposingly directed finger flanges extending outward from a rear end thereof;
(b) a boss fixedly attached to said barrel near said front end of said barrel;
(c) a barb fixedly attached to said barrel near said rear end of said barrel;
(d) a cylindrical sheath having a rear open end and a front open end and being slidingly received on said barrel and being movable between a retracted needle exposing position and an extended needle surrounding position; said sheath having a slot therein to receive said boss; said slot including a longitudinal portion extending axially along said barrel and a laterally extending portion extending laterally with respect to said barrel;
(e) a spring biasingly urging said sheath towards the extended needle surrounding position; said spring being secured to said barrel and said sheath such that said spring also biasingly urges said boss into said laterally extending portion of said slot as said sheath is advanced to said extended needle surrounding position such that when said boss is positioned in said laterally extending portion of said slot, said sheath may not be retracted by only the application of an axial force to said sheath but a user may rotate said sheath against said spring to allow retraction of said sheath relative to said barrel;
(f) said sheath includes a barb receiving aperture positioned near said rear open end thereof such that when said sheath is advanced to the retracted needle exposing position said barb receiving aperture encircles said barb so as to prevent said sheath from being advanced to the extended needle surrounding position; a pair of slits extend along said cylindrical sheath from said rear open end thereof on opposite sides of s id barb receiving aperture so as to form a tab; and
(g) a trigger integrally connected to said tab such that said trigger is engageable by a user so as to swing said barb receiving aperture out of encircling relationship with said barb so as to allow said spring to biasingly urge said cylindrical sheath to the extended needle surrounding position.

9. The syringe as disclosed in claim 8 wherein:
(a) said barb is positioned on said cylindrical syringe barrel between said finger flanges such that when said cylindrical sheath is restrained in the retracted needle exposing position said trigger is positioned between said finger flanges so as to be readily engageable by the thumb of a user grasping the finger flanges with the index finger and the middle finger.

10. The syringe as disclosed in claim 8 wherein:
(a) said sheath is made of a transparent, resilient plastic.

* * * * *